(12) United States Patent
Liou et al.

(10) Patent No.: US 9,400,250 B2
(45) Date of Patent: Jul. 26, 2016

(54) METHOD FOR ANALYZING MUSHROOMS

(71) Applicant: HAN SHENG BIOTECH CO., LTD., Pingtung County (TW)

(72) Inventors: Shorong-Shii Liou, Pingtung County (TW); I-Min Liu, Pingtung County (TW); Wen-Liang Lai, Pingtung County (TW); Jing-Wen Cao, Pingtung County (TW)

(73) Assignee: Han Sheng Biotech Co., Ltd., Changjhih Township, Pingtung County (TW)

( * ) Notice: Subject to any disclaimer, the term of this patent is extended or adjusted under 35 U.S.C. 154(b) by 295 days.

(21) Appl. No.: 14/041,512

(22) Filed: Sep. 30, 2013

(65) Prior Publication Data

US 2015/0090902 A1    Apr. 2, 2015

(51) Int. Cl.
*G01N 21/64* (2006.01)

(52) U.S. Cl.
CPC .... *G01N 21/6486* (2013.01); *G01N 2021/6421* (2013.01); *G01N 2021/6423* (2013.01)

(58) Field of Classification Search
CPC .......... G01N 21/6428; G01N 21/6486; G01N 33/025; G01N 2400/10; G01N 2333/37; G01N 33/5097
See application file for complete search history.

(56) References Cited

U.S. PATENT DOCUMENTS

| | | | |
|---|---|---|---|
| 6,563,122 B1 * | 5/2003 | Ludeker et al. | 250/458.1 |
| 2002/0142324 A1 * | 10/2002 | Wang et al. | 435/6 |
| 2005/0247868 A1 * | 11/2005 | Call et al. | 250/282 |
| 2008/0101657 A1 * | 5/2008 | Durkin et al. | 382/110 |
| 2011/0036995 A1 * | 2/2011 | Binnie et al. | 250/459.1 |
| 2013/0005607 A1 | 1/2013 | Van Wordragen et al. | |
| 2013/0284945 A1 * | 10/2013 | Aitkenhead et al. | 250/459.1 |

FOREIGN PATENT DOCUMENTS

| | | | |
|---|---|---|---|
| CN | 103529004 A | * | 1/2014 |
| EP | 2226336 A1 | | 8/2010 |

OTHER PUBLICATIONS

Jing et al., "Determination of fatty acids from mushrooms using high performance liquid chromatography with fluorescence detection and online mass spectrometry", Food Research International vol. 48, Issue 1, Aug. 2012, pp. 155-163.*

* cited by examiner

*Primary Examiner* — Marcus Taningco
(74) *Attorney, Agent, or Firm* — Muncy, Geissler, Olds & Lowe, P.C.

(57) ABSTRACT

The invention discloses a method for rapidly quantitative and qualitative analyzing active ingredients of mushrooms. The method for analyzing mushrooms uses a 3-D fluorescence-detecting system to analyze a sample of mushrooms, with an excitation wavelength and an emission wavelength being 250 nm and 310 nm, respectively.

3 Claims, 16 Drawing Sheets
(4 of 16 Drawing Sheet(s) Filed in Color)

METHOD FOR ANALYZING MUSHROOMS

BACKGROUND OF THE INVENTION

1. Field of the Invention

The present invention generally relates to a method for analyzing mushrooms and, more particularly, to a method, which used to rapidly analyze active ingredients of mushrooms.

2. Description of the Related Art

Mushrooms are rich in polysaccharides, which can stimulate activation of macrophages, secretion of TNF and IL-2, and production of antibodies, thereby possessing fine antitumor activity. Besides polysaccharides, *Taiwanofungus camphoratus*, one mushroom, contains more than 200 species of triterpenoids, which can possess effects such as anti-tumor, liver-protective, anti-dotal, anti-high blood lipid and pressure and immuno-modulating activities. As a result, *Taiwanofungus camphoratus* is believed to be a great choice for health care.

Due to excellent anti-tumor activities of the mushrooms, industries tend to develop several methods for culturing mushrooms or for extracting mushrooms, to improve amounts of active ingredients in mushroom extracts. However, conventional methods for analyzing mushrooms used to analyze the active ingredients in mushroom extracts have defaults discussed below.

In a conventional method for analyzing mushrooms, DNA of a sample of mushrooms is extracted, followed by a PCR reaction or a real-time PCR reaction to analyze DNA or mRNA of mushrooms. However, the conventional method for analyzing mushrooms can only be used to analyze species of mushrooms, but not be used to quantitatively or qualitatively analyze amounts of active ingredients of mushrooms.

In another conventional method for analyzing mushrooms, a sample of mushrooms is analyzed by a reversed phase chromatography using a C18 column, for example. The another conventional method for analyzing mushrooms can be used to quantitatively or qualitatively analyze amounts of active ingredients of mushrooms. However, during the process of the reversed phase chromatography, more time for analyzing is needed. Further, after analyzing one sample of mushrooms, additional time for washing the C18 column and for balancing the C18 column are further needed. That is, another conventional method for analyzing mushrooms with the reversed phase chromatography is not suitable for large-scale screening.

In light of this, it is necessary to improve the conventional method for analyzing mushrooms.

SUMMARY OF THE INVENTION

It is therefore the objective of this invention to provide a method for analyzing mushrooms to quantitatively and qualitatively analyze active ingredients of sample of mushrooms, further improving the quality of commercial mushroom products.

It is another objective of this invention to provide a method for analyzing mushrooms to quickly analyze active ingredients of sample of mushrooms, further saving time of analysis.

One embodiment of the invention discloses a method for analyzing mushrooms comprising: providing a sample of mushrooms; and analyzing the sample of mushrooms by a 3-D fluorescence-detecting system, wherein an excitation wavelength and an emission wavelength are 250 nm and 310 nm, respectively.

In a preferred form shown, before analyzing the sample of mushrooms by the 3-D fluorescence-detecting system, the sample of mushrooms is purified by a size-exclusion chromatography and obtained a purified sample of mushrooms, followed by analyzing the purified sample of mushrooms by the 3-D fluorescence-detecting system.

In the preferred form shown, molecular weight of the purified sample of mushrooms is between 100 Da to 10,000 Da.

In the preferred form shown, the sample of mushrooms is diluted to clearance and transparent, followed by filtrating by a 0.22 μm membrane.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

Figure 1:
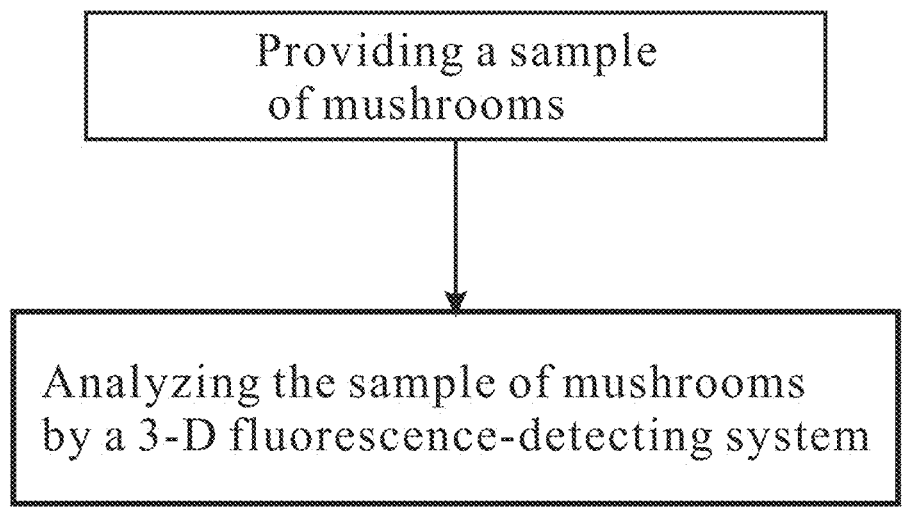
FIG. 1 is a flow chart of a method for analyzing mushrooms according to a first embodiment of the invention.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Referring to FIG. 1 being a flow chart of a method for analyzing mushrooms according to a first embodiment of the invention, the first embodiment of the invention comprises: providing a sample of mushrooms, and analyzing the sample of mushrooms by a 3-D fluorescent detecting system.

In detail, the sample of mushrooms can be obtained by extraction from mushrooms using a solvent being water or any kinds of organic solvents, thereby active ingredients of the mushrooms, such as polysaccharides or triterpenoids, dissolving in the solvent. Alternatively, the sample of mushrooms also can be obtained by extraction using a supercritical carbon oxide fluid.

Preferably, the sample of mushrooms is diluted by the solvent used to extract the mushrooms until an appearance of the sample of mushrooms is clearance and transparent. The sample of mushrooms with the appearance being clearance and transparent is further filtrated by a 0.22 μm membrane to prevent colors or polysaccharides particulates of the sample of mushrooms from affecting results of following analysis.

Then, the sample of mushrooms is analyzed by a 3-D fluorescent detecting system with initial and final excitation wavelength being 200 to 900 nm, with initial and final emission wavelength being 200 to 900 nm, with slits of excitation and emission being 10 nm, with scanning speed being 30,000 nm/min, with photomultiplier being 700 V. Preferably, the excitation wavelength and the emission wavelength are set at 250 nm and 310 nm, respectively.

In order to prove the method for analyzing mushrooms of the first embodiment is capable of quantitative and qualitative analyzing active ingredients of the sample of mushrooms, an extract of *Taiwanofungus camphoratus* is used to be the sample of mushrooms. The extract of *Taiwanofungus camphoratus* is obtained as following. A powder of *Taiwanofungus camphoratus* is extracted with an ethanol solvent for three times to obtain a stock solution, wherein the concentration of the ethanol solvent is 95%, wherein a weight to volume ratio of the power to the ethanol solvent is 1:1. The stock solution is further concentrated to obtain the extract of *Taiwanofungus camphoratus*.

Referring to Table 1, the extract of *Taiwanofungus camphoratus* is 10-fold serial diluted with the ethanol solvent. Groups A1, A2, A3 and A4 are 10-fold, 100-fold, 1,000-fold and 10,000-fold diluents of the extract of *Taiwanofungus camphoratus*, respectively. Each of the diluents has total volume being 50 mL, while 15 mL of the diluents is held in centrifugal tubes, separately. Remained diluents are further filtrated by 0.22 μm membranes being tolerant of ethanol (cellulose acetate ester membrane purchased form Advantec MFS Inc., USA) to obtain filtrates named groups B1, B2, B3 and B4, respectively.

TABLE 1

| the diluents and the filtrates with different dilution fold used in the experiment | | |
|---|---|---|
| Dilution fold | Diluents | Filtrates |
| 10-fold | A1 | B1 |
| 100-fold | A2 | B2 |
| 1,000-fold | A3 | B3 |
| 10,000-fold | A4 | B4 |

Figures 2A, 2B:
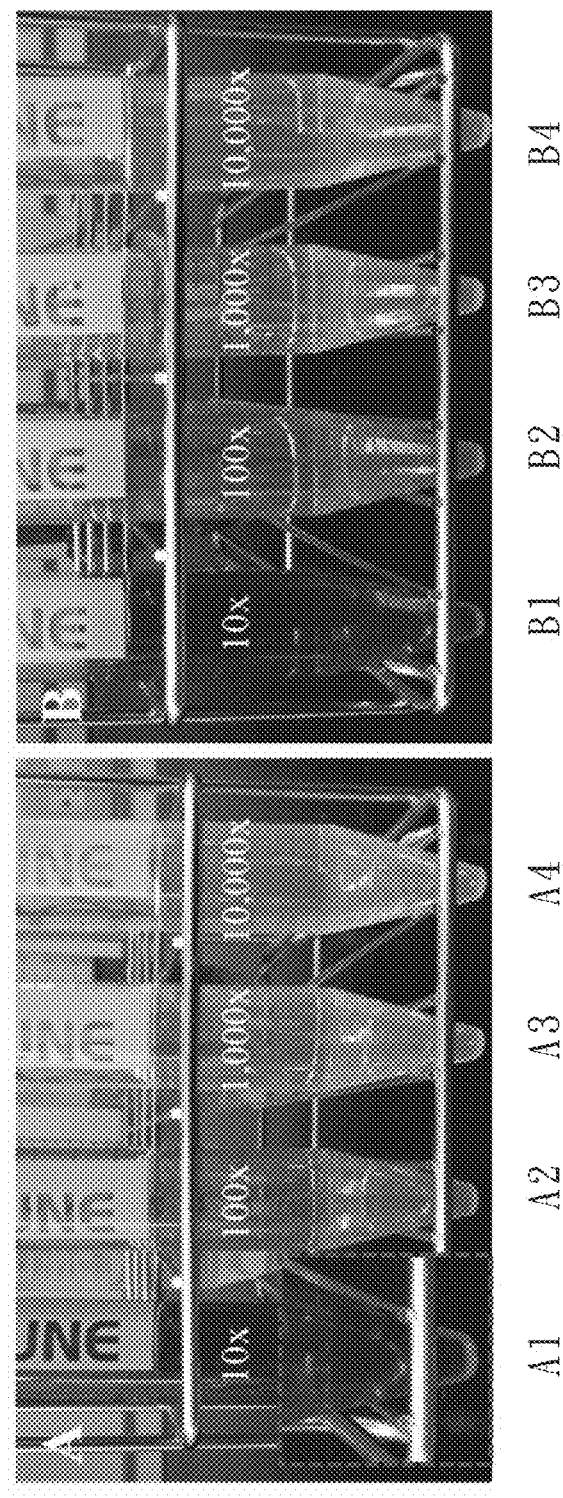
FIG. 2A is an appearance view of diluents of *Taiwanofungus camphoratus* according to Table 1.
FIG. 2B is an appearance view of filtrates of *Taiwanofungus camphoratus* according to Table 1.

Referring to FIG. 2A, the diluent being group A1 shows apparent precipitation after standing. As the dilution fold increases, color of the diluents changes from brown (group A1), yellow (group A2), light yellow (group A3) to transparent (group A4). Further, referring to FIG. 2B, the filtrate of group B1 also show apparent precipitation after standing. Besides, color of the filtrates also changes from brown (group B1), yellow (group B2), light yellow (group B3) to transparent (group B4).

Figure 3:
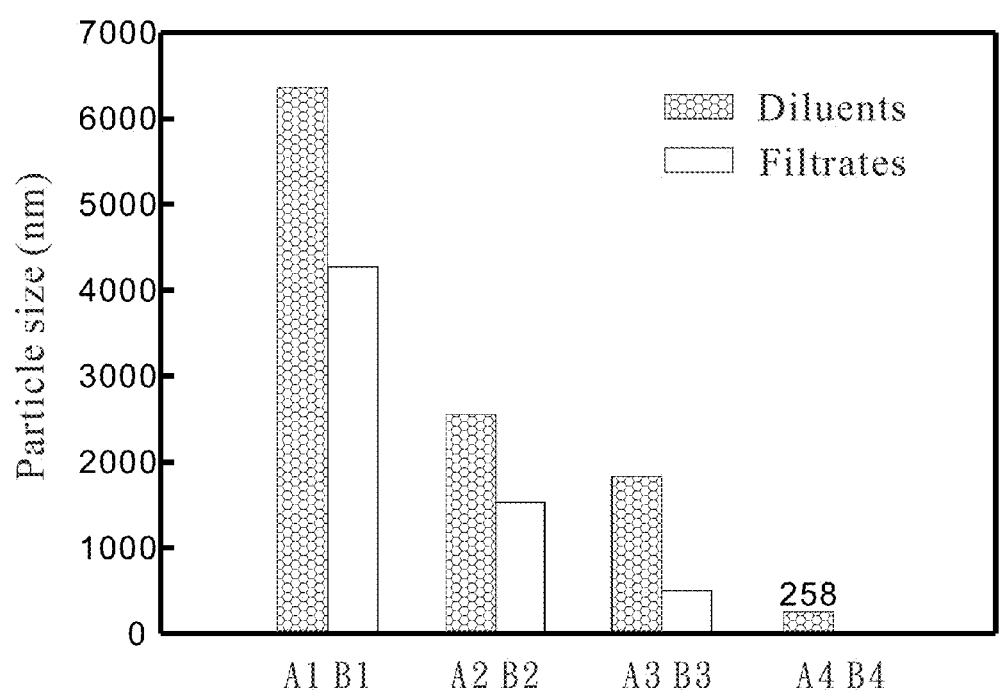
FIG. 3 is a bar chart showing distribution of particle sizes of the dilutes or filtrates of *Taiwanofungus camphoratus* according to Table 1.

Furthermore, a particle size analyzer is used to analyze particle sizes of the diluents (groups A1-A4) and the filtrates (groups B1-B4). Referring to FIG. 3, a particle size of group A1 is up to 6,000 nm, while a particle size of group B1 filtrated by the 0.22 μm membrane is still up to 4,000 nm. Groups A3 and B3 being 1,000-fold dilution with or without filtration show particle sizes of 2,000 and 500 nm, respectively. Group A4 with 10,000-fold dilution has a particle size being 258 nm, and group B4 further filtrated by the 0.22 μm membrane has a particle size under a detection limit of the particle size analyzer, showing that particulates is obviously removed in group B4 and further preventing the particulates from affecting analyzing results.

Figure 4:
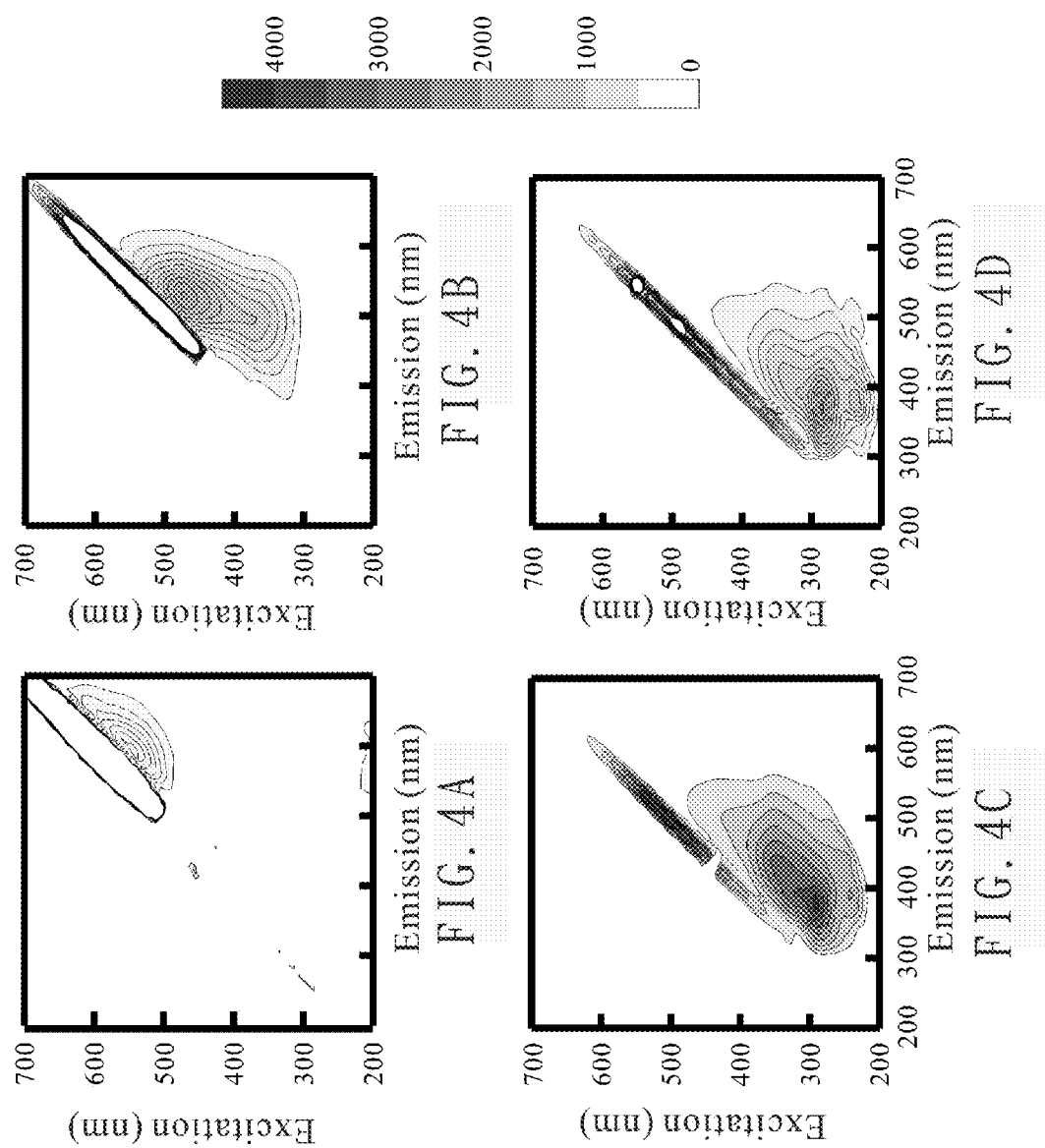
FIG. 4A is an EEM fluorescence spectra of the dilute being group A1 according to Table 1.
FIG. 4B is an EEM fluorescence spectra of the dilute being group A2 according to Table 1.
FIG. 4C is an EEM fluorescence spectra of the dilute being group A3 according to Table 1.
FIG. 4D is an EEM fluorescence spectra of the dilute being group A4 according to Table 1.

Besides, the dilutes of groups A1 to A4 are analyzed by the 3-D fluorescent detecting system, and results are shown in FIGS. 4A to 4D, respectively. As the dilution fold increases, peak of the dilutes apparently moves to low excitation/emission wavelength. Furthermore, group A4 with 10,000-fold dilution has an excitation/emission peak at 290/380 nm with fluorescence intensities being 2,265 as shown in FIG. 4D.

Figure 5:
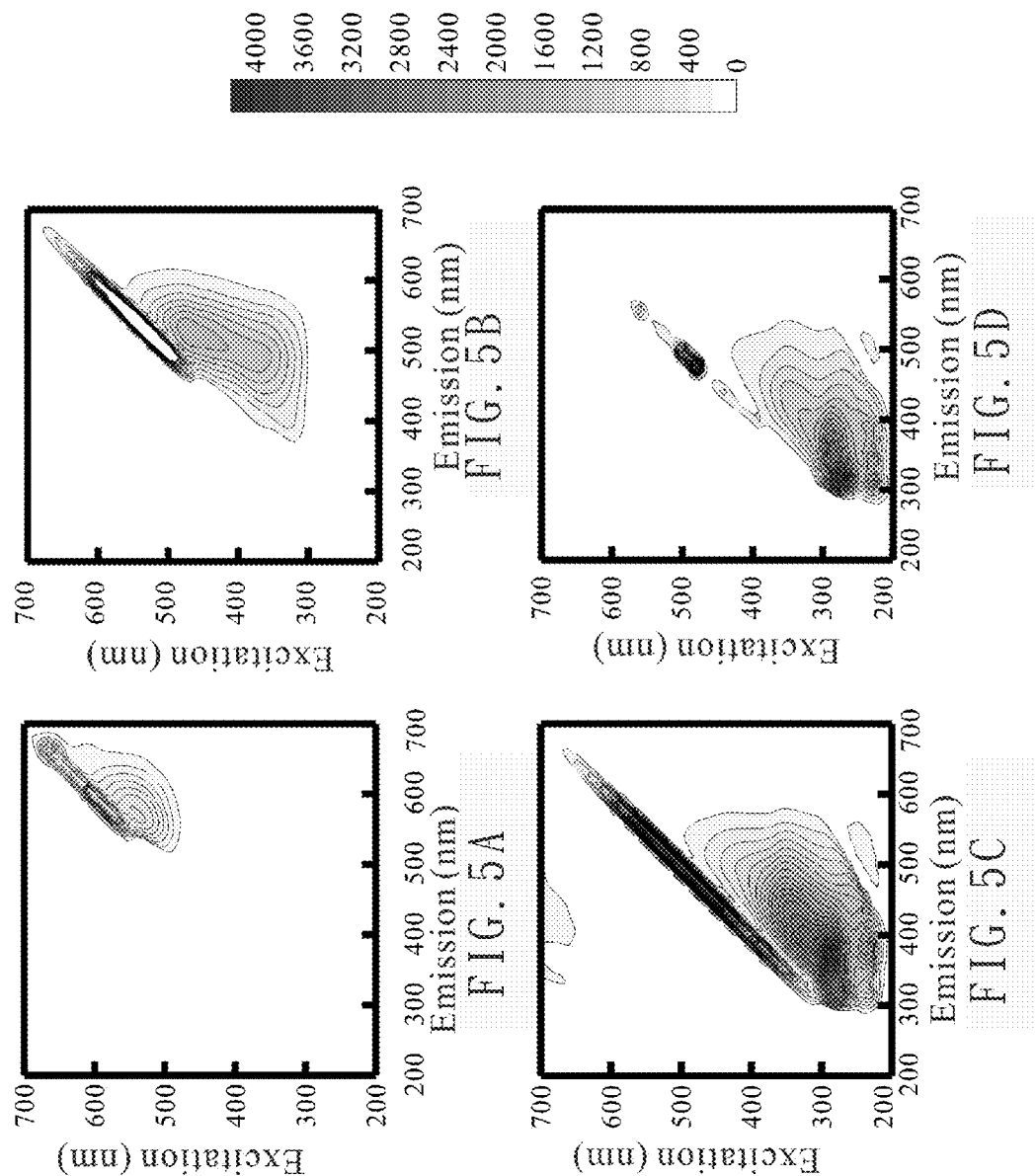
FIG. 5A is an EEM fluorescence spectra of the filtrate being group B1 according to Table 1.
FIG. 5B is an EEM fluorescence spectra of the filtrate being group B2 according to Table 1.
FIG. 5C is an EEM fluorescence spectra of the filtrate being group B3 according to Table 1.
FIG. 5D is an EEM fluorescence spectra of the filtrate being group B4 according to Table 1.

Moreover, the filtrates of groups B1 to B4 are also analyzed by the 3-D fluorescent detecting system, and results are shown in FIGS. 5A to 5D, respectively. Group B4 with 10,000-fold dilution has an excitation/emission peaks at 270/320 nm with fluorescence intensities being 3,128 as shown in FIG. 5D. That is, in order to increase accuracy of results, the extract of *Taiwanofungus camphoratus* preferably undergoes dilution and filtration before analyzing by the 3-D fluorescent detecting system.

Figure 6:
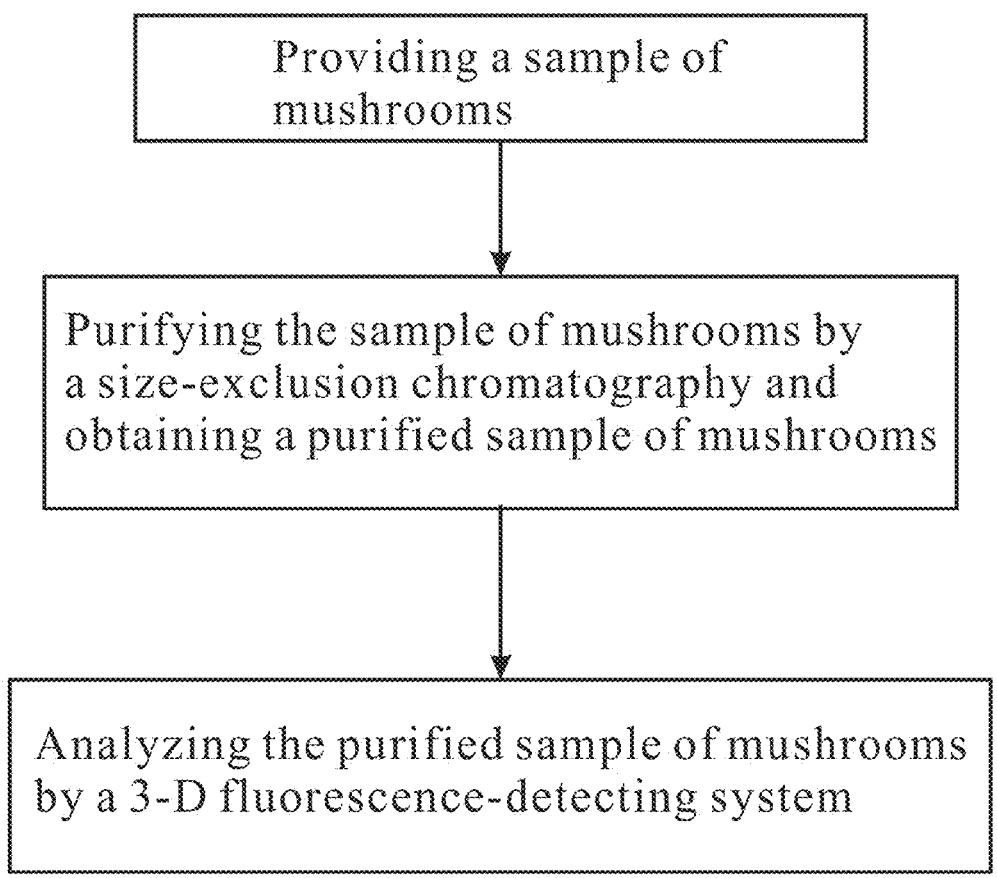
FIG. 6 is a flow chart of a method for analyzing mushrooms according to a second embodiment of the invention.

FIG. 6 shows a flow chart of a method for analyzing mushrooms according to a second embodiment of the invention. In comparison with the first embodiment of the invention, before analyzing the sample of mushrooms by the 3-D fluorescence-detecting system, the second embodiment of the invention the sample of mushrooms is further purified by a size-exclusion chromatography and obtained a purified sample of mushrooms.

In detail, organic substances are determined by the size-exclusion chromatography combined with a diode array detector to scan for whole wavelengths. Moreover, molecular weight of the purified sample of mushrooms is 100 to 10,000 Da. The purified sample of mushrooms is further analyzed by the 3-D fluorescence-detecting system.

In order to prove the method for analyzing mushrooms of the second embodiment is capable of quantitative and qualitative analyzing active ingredients of the sample of mushrooms, the filtrate being group B4 is used to be the sample of mushrooms.

In the second embodiment of the invention, the size-exclusion chromatography is chose to be a liquid chromatography being L-7100 purchased form Hitachi, Japan, and further combine with the diode array detector to detect signals of the organic substances. Preferably, the size-exclusion chromatography is carried out in a column being TSK HW-55S purchased from Tosoh, USA with inner diameter and length being 7.8 and 300 mm, respectively. Besides, the column is packing with hydroxylated methacrylic polymer with particle size and pore size being 20-40 μm and 125 Å, respectively. A flow rate of the size-exclusion chromatography is 0.5 mL/min, and a mobile phase is phosphate buffer formulated with 2.4 mM $NaH_2PO4$, 1.6 $Na_2HPO_4$ and 25 mM $Na_2SO_4$, with ionic strength being 100 mM.

Figure 7:
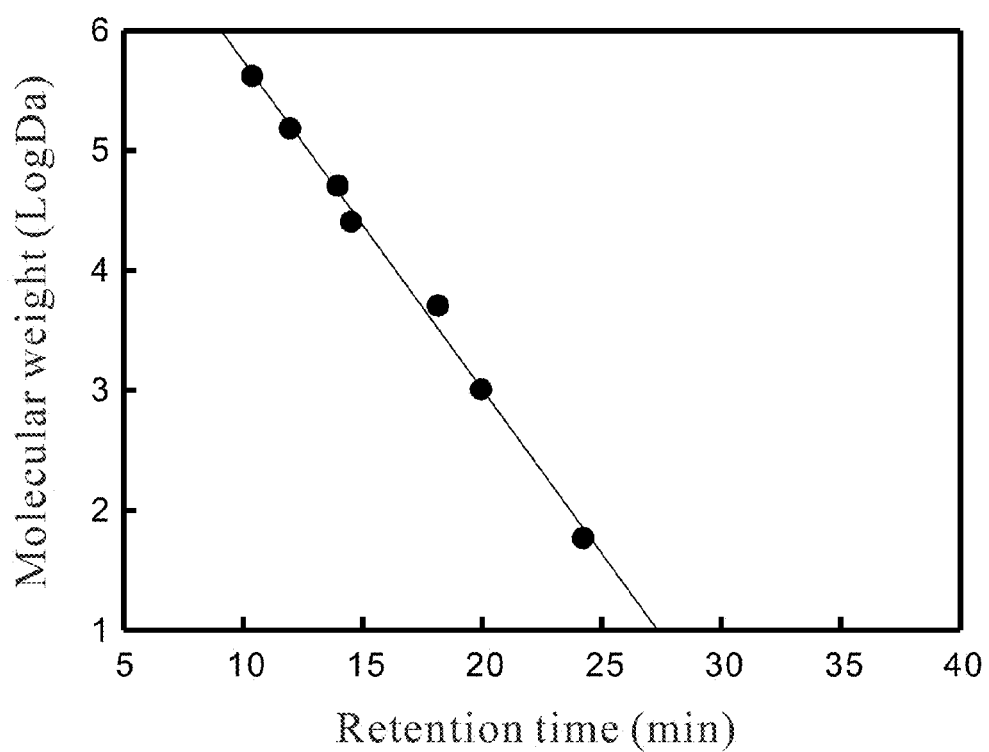
FIG. 7 is a calibration curve with molecular weight versus retention time of Molecular-weight size markers and acetone.

Besides, in the second embodiment of the invention, molecular-weight size markers with molecular weight being 410,000, 150,000, 50,000, 25,000, 50,000 and 1,000 Da and acetone with molecular weight being 58 are used to plot a calibration curve with molecular weight versus retention time, shown in FIG. 7. Furthermore, the calibration curve has a regression curve with formula being Log(M)=8,336−0.263×Ve (R=0.997). The regression curve will be further used to calculate corresponding molecular weight of the active ingredients of the sample of mushrooms.

Figure 8:
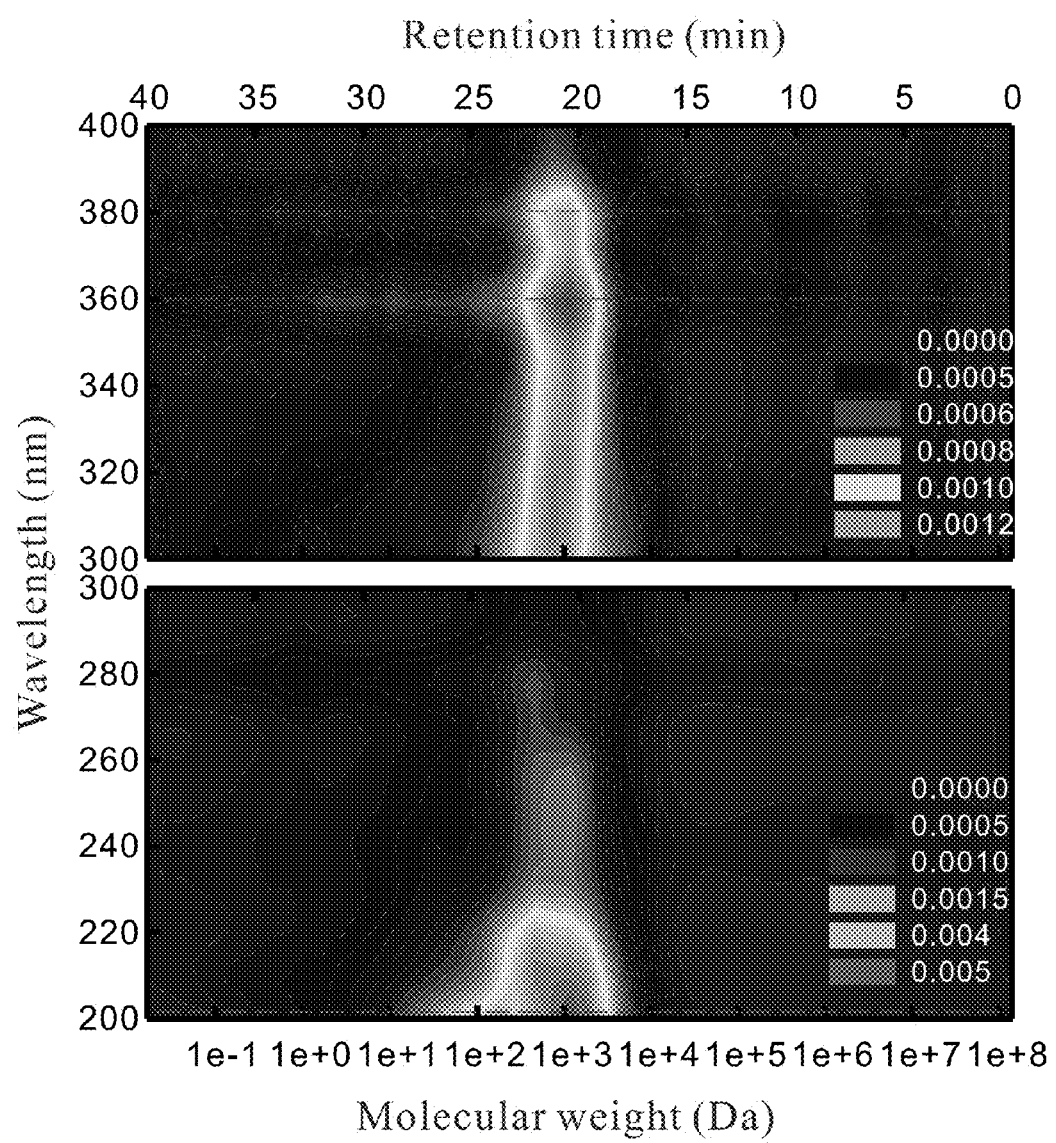
FIG. 8 is a SEC chromatogram of the filtrate being group B4 according to Table 1.

Referring to FIG. 8, the filtrate being group B4 is analyzed and purified by the size-exclusion chromatography, which purified eluate shows an apparent peak with retention time being 19-25 min and molecular weight being $10^2$-$10^4$ Da.

Figure 9:
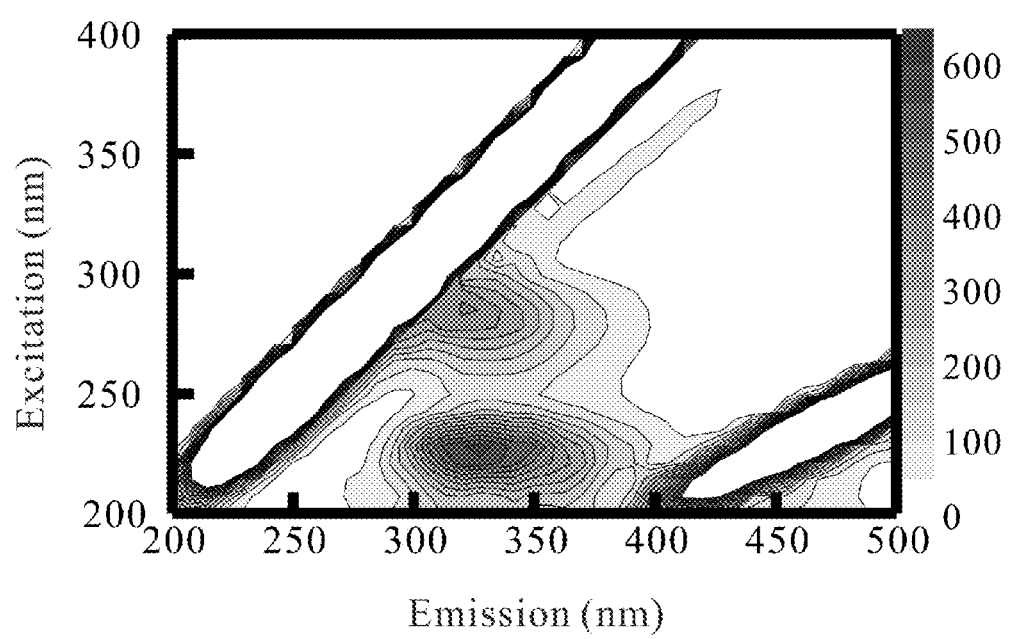
FIG. 9 is an EEM fluorescence spectrum of the filtrate being group B4 according to Table 1.

Besides, the purified eluate flows into the 3-D fluorescent detecting system through a flow cell and organic substances of the purified eluate at 23 min are analyzed by the 3-D fluorescent detecting system. As shown in FIG. 9, two peaks at 230/320 nm and 290/320 nm (excitation/emission) appear with fluorescence intensities being 628.4 and 490.9, respectively.

In order to prove the results analyzed by the second embodiment of the invention are marker components of *Taiwanofungus camphoratus* being 4,7-dimethoxy-5-methyl-1,3-benzodioxole and dehydrosulphurenic acid. Further analysis of the two marker components of *Taiwanofungus camphoratus* with concentration being 20 ppm is performed.

Figure 10A:
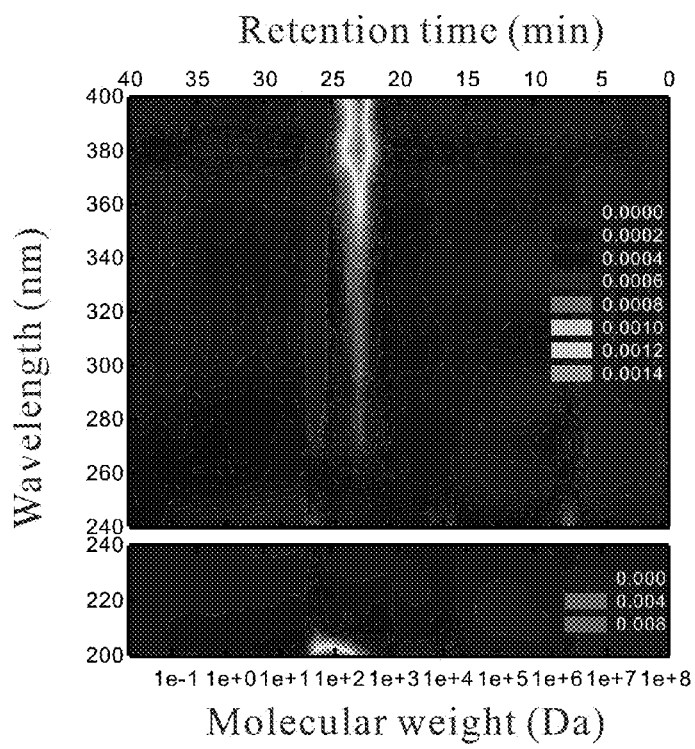
FIG. 10A is a SEC chromatogram of a marker component of *Taiwanofungus camphoratus* being 4,7-dimethoxy-5-methyl-1,3-benzodioxole.
Figure 10B:
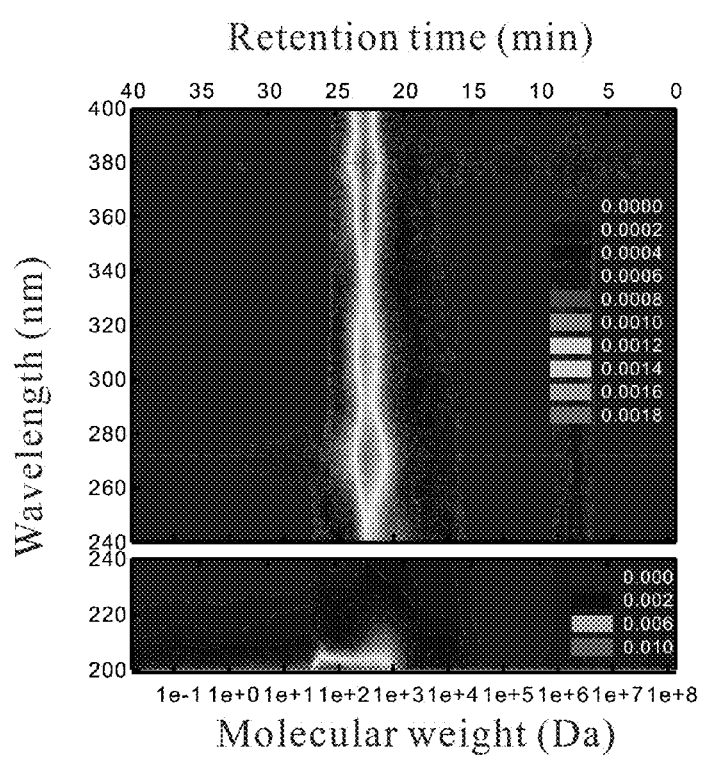
FIG. 10B is a SEC chromatogram of a marker component of *Taiwanofungus camphoratus* being dehydrosulphurenic acid.

Referring to FIGS. 10A and 10B being SEC chromatograms of the two marker components of *Taiwanofungus camphoratus* being 4,7-dimethoxy-5-methyl-1,3-benzodioxole and dehydrosulphurenic acid, respectively. Peaks appear at 20-25 min with molecular weights being $10^2$-$10^3$ Da. Furthermore, the peak of the marker component being 4,7-dimethoxy-5-methyl-1,3-benzodioxole shows absorbance at 200 and 380 nm, while the peak of the marker component being dehydrosulphurenic acid shows absorbance at 270, 310 and 380 nm. That is, the two marker components of *Taiwanofungus camphoratus* have similar molecular weight but different absorbent wavelength. Therefore, the different absorbent wavelengths of the two marker components of *Taiwanofungus camphoratus* are suitable for distinguishing. Moreover, compared with FIG. 8, the extract of *Taiwanofungus camphoratus* comprises the two marker components being 4,7-dimethoxy-5-methyl-1,3-benzodioxole and dehydrosulphurenic acid.

Figures 11A, 11B:
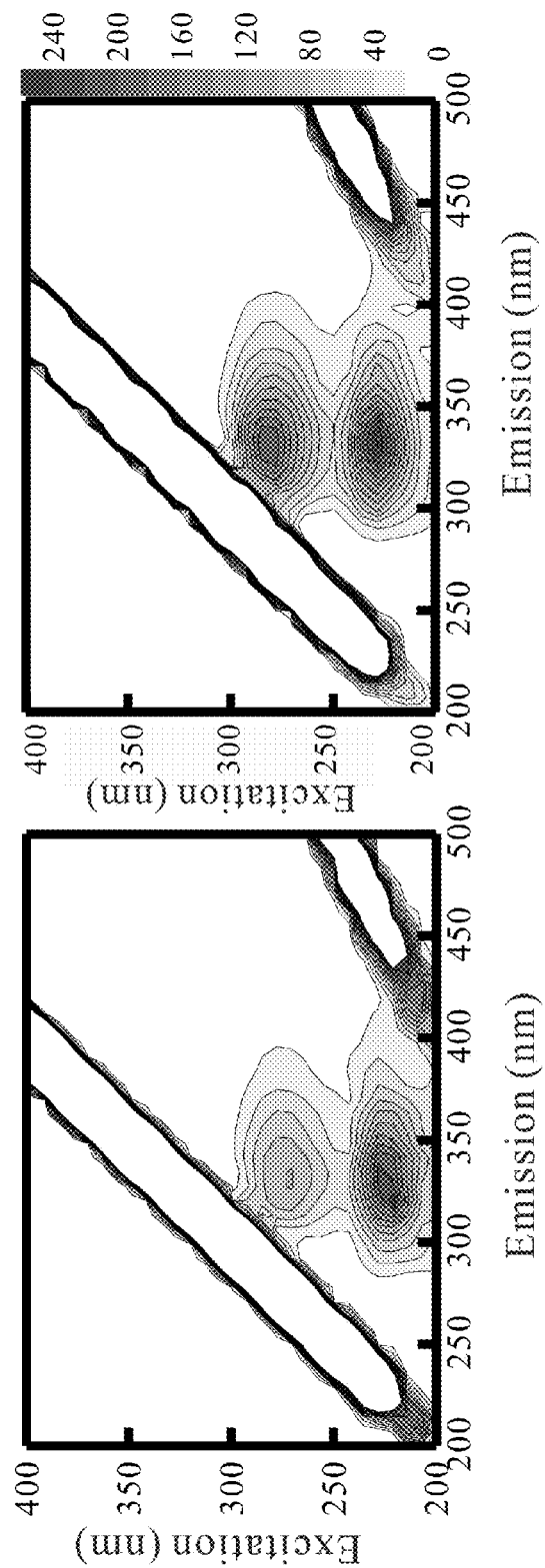
FIG. 11A is an EEM fluorescence spectrum of a marker component of *Taiwanofungus camphoratus* being 4,7-dimethoxy-5-methyl-1,3-benzodioxole.
FIG. 11B is an EEM fluorescence spectrum of a marker component of *Taiwanofungus camphoratus* being dehydrosulphurenic acid.

Moreover, purified eluates of the two marker components with retention time being 23 min and corresponding molecular weights being 100-200 Da are analyzed by the 3-D fluorescent detecting system. As shown in FIG. 11A, peaks of 4,7-dimethoxy-5-methyl-1,3-benzodioxole at 220/320 and 270/330 nm (excitation/emission) have fluorescent intensities being 243.7 and 104.5, respectively. Besides, referring to FIG. 11B, peaks of dehydrosulphurenic acid at 230/330 and 280/330 nm (excitation/emission) have fluorescent intensities being 285.3 and 125.6, respectively. Moreover, compared with FIG. 9, the extract of *Taiwanofungus camphoratus* comprises the two marker components being 4,7-dimethoxy-5-methyl-1,3-benzodioxole and dehydrosulphurenic acid.

Figure 12A:
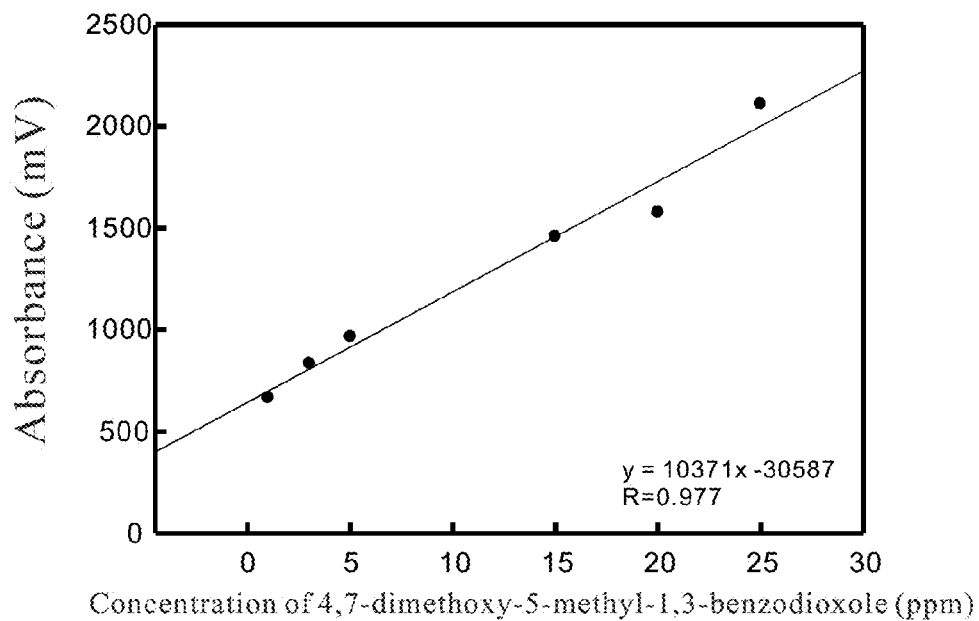
FIG. 12A is a calibration curve with absorbance at 205 nm versus concentrations of a marker component of *Taiwanofungus camphoratus* being 4,7-dimethoxy-5-methyl-1,3-benzodioxole.
Figure 12B:
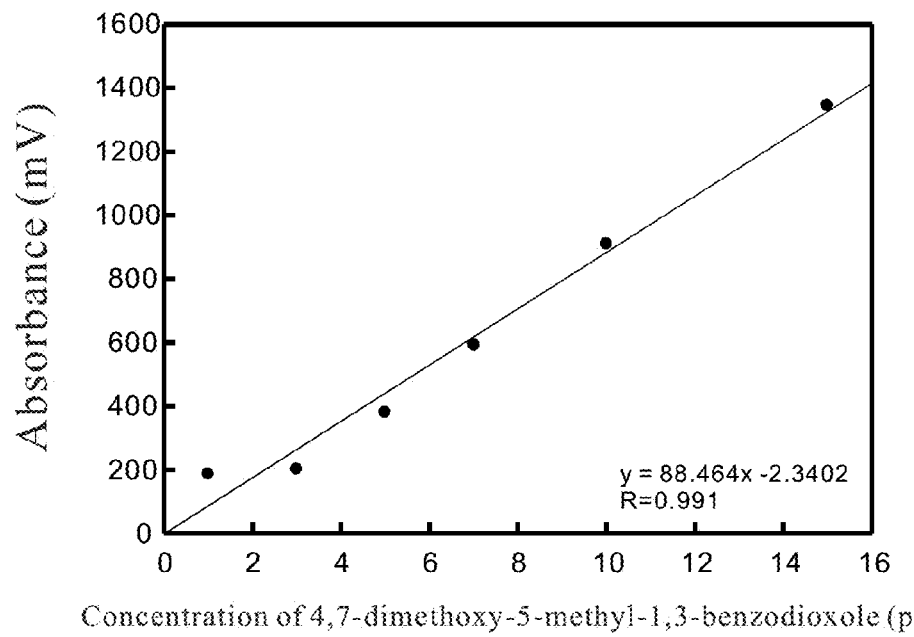
FIG. 12B is a calibration curve with absorbance at 380 nm versus concentrations of a marker component of *Taiwanofungus camphoratus* being 4,7-dimethoxy-5-methyl-1,3-benzodioxole.
Figure 12C:
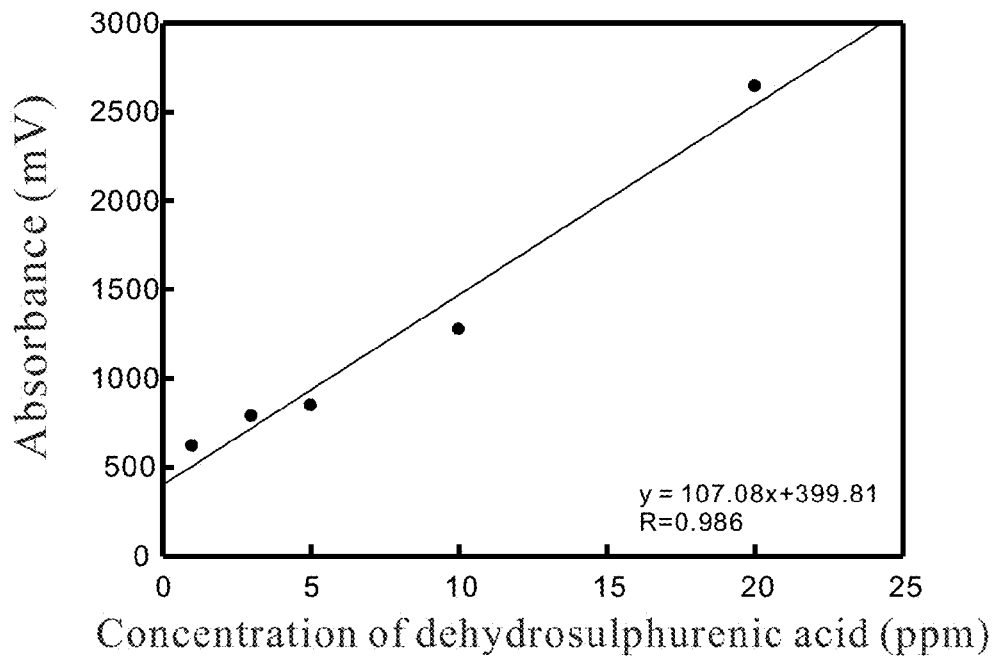
FIG. 12C is a calibration curve with absorbance at 205 nm versus concentrations of a marker component of *Taiwanofungus camphoratus* being dehydrosulphurenic acid.
Figure 12D:
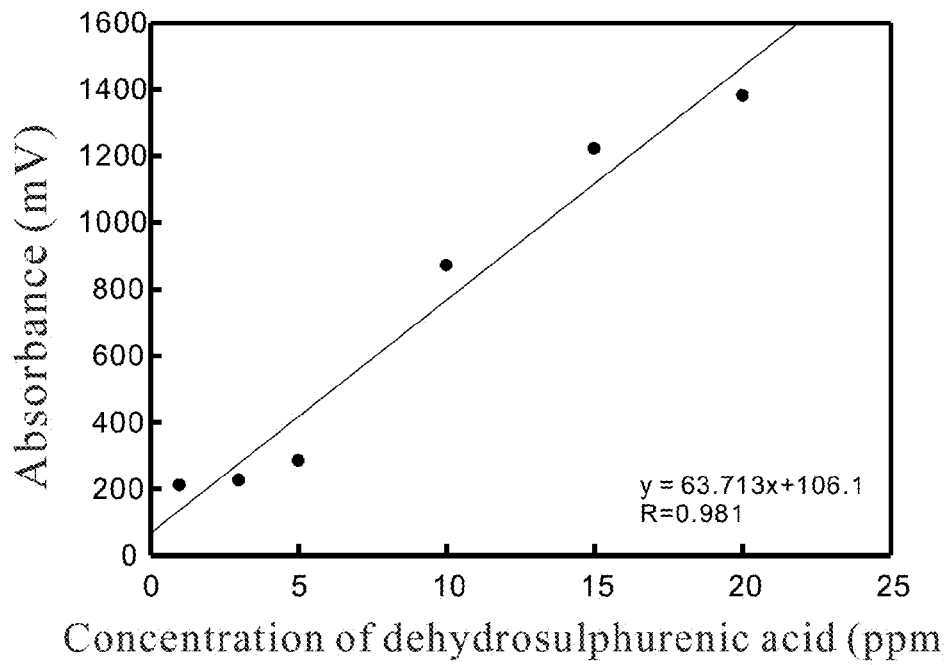
FIG. 12D is a calibration curve with absorbance at 380 nm versus concentrations of a marker component of *Taiwanofungus camphoratus* being dehydrosulphurenic acid.

The results of the two marker component of *Taiwanofungus camphoratus* shows main retention time being 23 min and absorbent wavelength being 205 and 380 nm. Further, calibration curves with absorbance versus concentration are plotted as in FIGS. 12A-12D, respectively. The calibration curves of 4,7-dimethoxy-5-methyl-1,3-benzodioxole (FIGS. 12A-12B) and dehydrosulphurenic acid (FIGS. 12C-12D) has a better linearity between concentration being 1-25 ppm. According to the calibration curves and its corresponding regression curves shown in FIGS. 12A-12D, concentrations of 4,7-dimethoxy-5-methyl-1,3-benzodioxole and dehydrosulphurenic acid of the dilute of group B4 shown in FIG. 9 can be measured. That is, 4,7-dimethoxy-5-methyl-1,3-benzodioxole has a concentration being 31,514 ppm at the absorbent wavelength being 205 nm and a concentration being 44,802 ppm at the absorbent wavelength being 380 nm, while dehydrosulphurenic acid has concentrations being 49,747 and 45,187 ppm at the absorbent wavelength being 205 and 380 nm, respectively.

Figure 13:
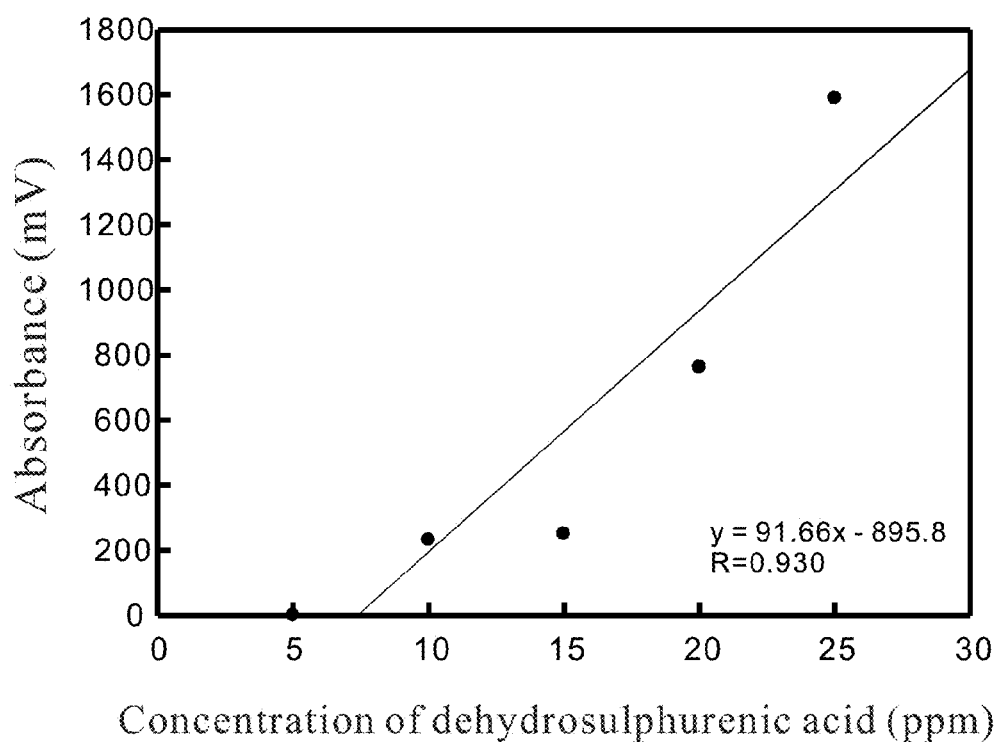
FIG. 13 is a calibration curve with absorbance at 270 nm versus concentrations of a marker component of *Taiwanofungus camphoratus* being dehydrosulphurenic acid.

Also, dehydrosulphurenic acid with concentration more than 10 ppm shows a peak at the absorbent wavelength being 270 nm. Another calibration curve and its corresponding regression curve are plotted and shown in FIG. 13, and thereby calculating a concentration of the filtrate of group B4 shown in FIG. 9 as being 170.500 ppm.

Moreover, a marker component of *Cordyceps sinensis* being 3-deoxyadenosine with concentration being 10 ppm is also used to be the sample of mushrooms analyzed by the second embodiment of the invention.

Figure 14:
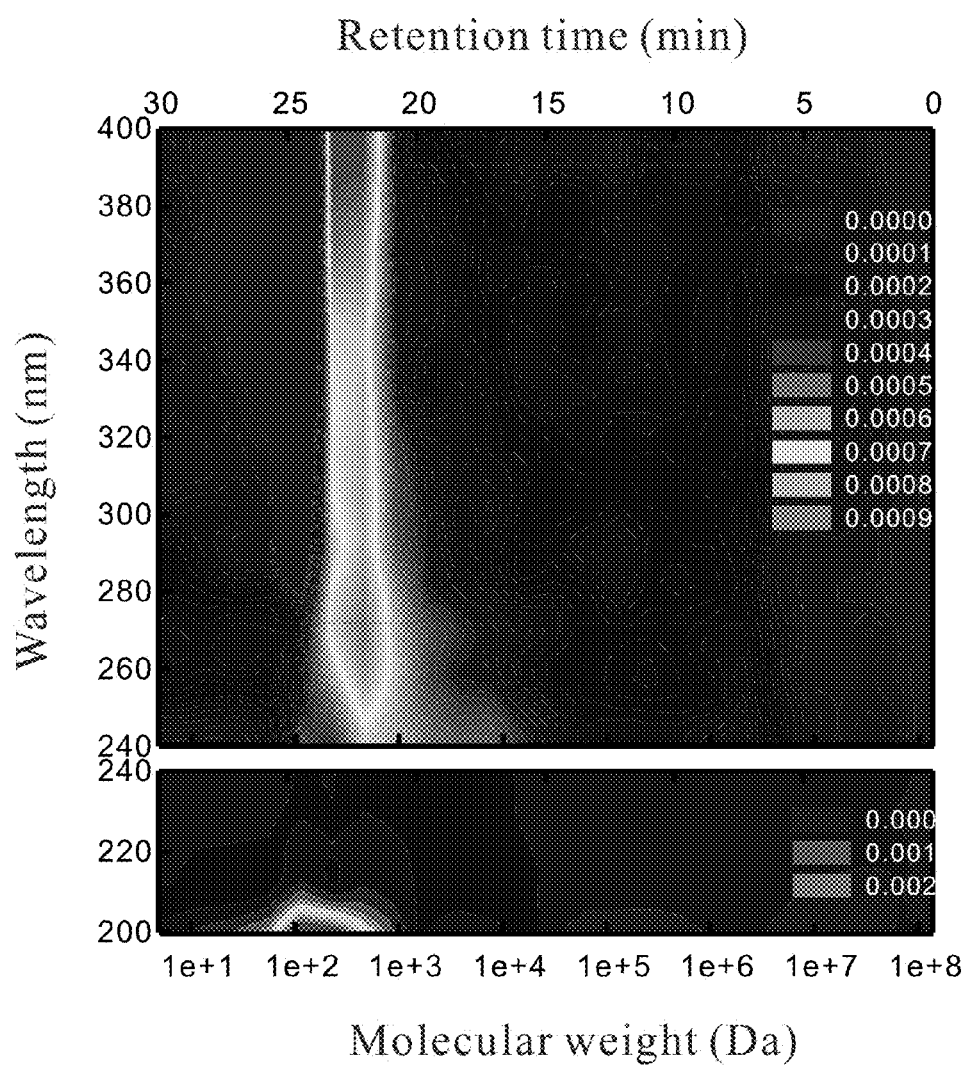
FIG. 14 is a SEC chromatogram of a marker component of *Cordyceps sinensis* being 3-deoxyadenosine.
Figure 15:
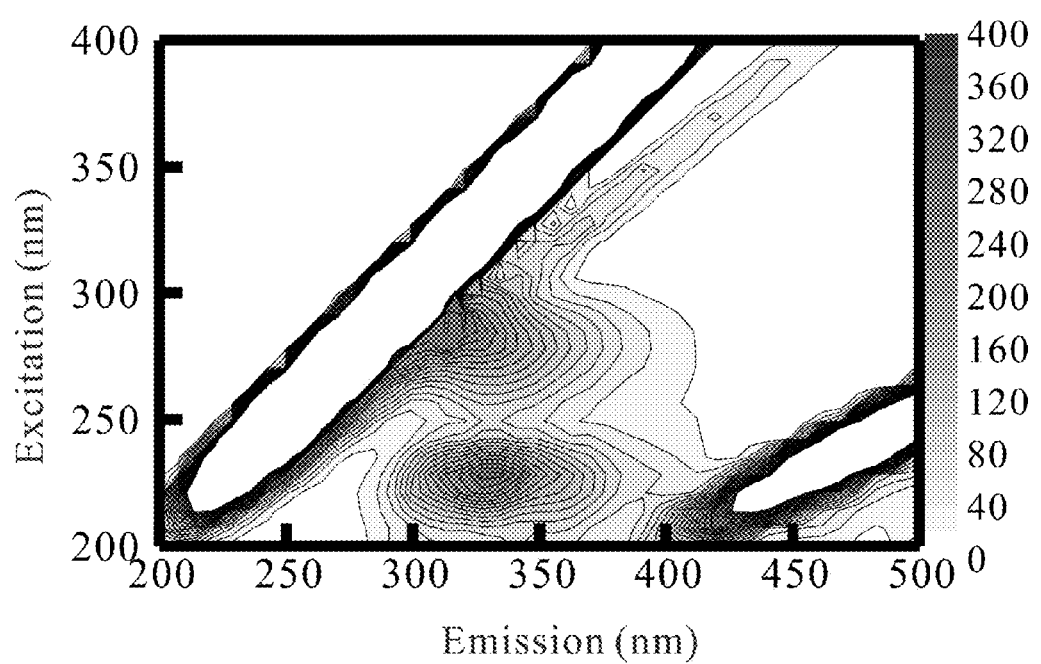
FIG. 15 is an EEM fluorescence spectrum of a marker component of *Cordyceps sinensis* being 3-deoxyadenosine.

FIG. 14 shows a SEC chromatogram of 3-deoxyadenosine by the size-exclusion chromatography. Further, purified eluate of 3-deoxyadenosine is further analyzed by the 3-D fluorescent detecting system (shown in FIG. 15). As a result, 3-deoxyadenosine has peaks at 290/320 and 230/330 nm (excitation/emission) with fluorescent intensities being 384.1 and 335.5, respectively. Thus, the second embodiment of the invention can also be used to analyze the marker of *Cordyceps sinensis* being 3-deoxyadenosine.

In conclusion, by detecting features of molecular structures, the method for analyzing mushrooms of the invention can rapidly quantitative and qualitative analyze active ingredients of the sample of mushrooms, thereby improving the quality of commercial mushrooms products.

Moreover, by calculating amounts of active ingredients according to excitation and emission wavelengths of the molecular structures of the sample of mushrooms, the method for analyzing mushrooms of the invention can reduce time for detection and analysis, thereby rapidly analyzing the sample of Mushrooms.

Although the invention has been described in detail with reference its presently preferable embodiment, it will be understood by one of ordinary skill in the art that various modifications can be made without departing from the spirit and the scope of the invention, as set forth in the appended claims.

What is claimed is:

1. A method for analyzing mushrooms comprising:
   providing a sample of mushrooms;
   purifying the sample of mushrooms by a size-exclusion chromatography to obtain a purified sample of mushrooms; and
   analyzing the purified sample of mushrooms by a 3-D fluorescence-detecting system, wherein an excitation wavelength and an emission wavelength are 250 nm and 310 nm, respectively.

2. The method for analyzing mushrooms as claimed in claim 1, with molecular weight of the purified sample of mushrooms is between 100 Da to 10,000 Da.

3. The method for analyzing mushrooms as claimed in claim 1, wherein the sample of mushrooms is diluted to clearance and transparent, followed by filtrating by a 0.22 μm membrane.

* * * * *